United States Patent [19]

Guigues et al.

[11] 4,256,480
[45] Mar. 17, 1981

[54] ISOXAZOLYL-ALKYL THIOCARBAMATES AND HERBICIDAL COMPOSITIONS THEREOF

[75] Inventors: François Guigues, Rillieux; Jacqueline Mourier; Daniel Demozay, both of Lyon, all of France

[73] Assignee: Philagro, Lyon, France

[21] Appl. No.: 909,645

[22] Filed: May 25, 1978

[30] Foreign Application Priority Data

May 31, 1977 [FR] France ................... 77 17455

[51] Int. Cl.³ .................. A01N 47/12; C07D 261/08
[52] U.S. Cl. ............................................ 71/88; 71/94; 71/95; 260/245.5; 544/137; 546/209; 546/245; 548/247; 548/249
[58] Field of Search ............ 71/88, 100; 260/307 DA, 260/307 H; 548/247

[56] References Cited

U.S. PATENT DOCUMENTS

| | | | |
|---|---|---|---|
| 2,992,091 | 7/1961 | Harman et al. ................... | 71/100 |
| 3,015,551 | 1/1962 | Godfrey et al. ................... | 71/88 |
| 3,166,565 | 1/1965 | Rigterink ......................... | 71/87 |
| 3,419,620 | 12/1968 | Becher et al. ..................... | 71/87 |
| 3,544,580 | 12/1970 | Lewis et al. ..................... | 260/302 A |
| 3,579,525 | 5/1971 | Tilles et al. ..................... | 71/94 |
| 3,743,498 | 7/1973 | Brantley ......................... | 71/88 |
| 3,877,921 | 4/1975 | Timmons et al. ................... | 71/88 |
| 4,028,376 | 6/1977 | Yukinaga et al. ................... | 71/88 |
| 4,124,591 | 11/1978 | Eicken et al. ..................... | 71/88 |

OTHER PUBLICATIONS

Scherer et al., "Pesticidal S-(isoxapolylmethyl) etc.," (1970) CA 73 No. 77235v. (1970).

*Primary Examiner*—Glennon H. Hollrah
*Attorney, Agent, or Firm*—Robert E. Burns; Emmanuel J. Lobato; Bruce L. Adams

[57] ABSTRACT

Novel isoxazolyl-alkyl thiolcarbamates and novel herbicidal compositions containing the novel thiolcarbamates are disclosed wherein the thiolcarbamates are of the formula:

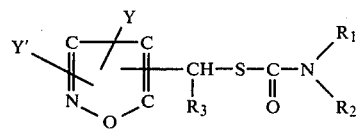

in which $R_1$ and $R_2$ are identical or different and each represents a hydrogen atom, a linear or branched alkyl radical containing 1 to 6 carbon atoms, a cycloalkyl radical containing 3 to 6 carbon atoms, an alkenyl radical containing 2 to 4 carbon atoms, an alkoxy radical containing 1 to 6 carbon atoms, an alkoxyalkyl radical in which each alkyl part contains 1 to 4 carbon atoms, an optionally substituted aryl radical, an optionally substituted aralkyl radical in which the alkyl part contains 1 to 4 carbon atoms, or a saturated or unsaturated heterocyclic radical which has 5 to 6 chain members and contains, as the hetero-atom, an oxygen, nitrogen or sulphur atom, or $R_1$ and $R_2$ together with the nitrogen atom to which they are bonded form a saturated or unsaturated, optionally substituted heterocyclic structure which has 5 to 6 chain members and can contain, as a hetero-atom, an oxygen atom in addition to the nitrogen atom, $R_3$ represents a hydrogen atom or an alkyl radical containing 1 to 4 carbon atoms and Y and Y' are identical or different and each represents a hydrogen or halogen atom, an alkyl radical containing 1 to 6 carbon atoms, a trifluoromethyl radical or an optionally substituted aryl radical. The new thiolcarbamates are useful in the form of herbicidal compositions for the selective destruction of weeds in crops of maize, groundnuts, rape, cotton, soya, beans, sunflowers, wheat and rice.

6 Claims, No Drawings

ISOXAZOLYL-ALKYL THIOCARBAMATES AND HERBICIDAL COMPOSITIONS THEREOF

BACKGROUND OF THE INVENTION

The invention relates to novel isoxazolyl-alkyl thiolcarbamates. It also relates to herbicidal compositions containing these compounds and to the processes for the selective destruction of weeds by means of these compositions.

French Patent Application No. 2,205,514 claims derivatives of thiolcarbamic acid and of dithiolcarbamic acid which are biodegradable herbicides and are of the general formula:

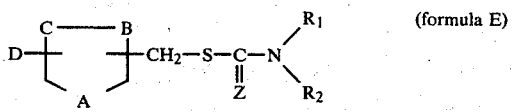

(formula E)

in which: A, B and C are identical or different and represent oxygen, nitrogen or sulphur atoms, —CH— chain members, or $NR_3$ radicals (in which $R_3$ represents a hydrogen atom or an alkyl radical), Z represents an oxygen or sulphur atom, D represents a halogen or an alkyl radical, $NO_2$ or $SR_4$ ($R_4$=H or alkyl) and $R_1$ and $R_2$ are identical or different and represent H or a lower alkyl.

This general formula E encompasses a very large number of compounds belonging to several different chemical families. The only compounds described in the examples illustrating this application are imidazolyl-alkyl thiolcarbamates, oxadiazolyl-alkyl-thiolcarbamates and thiazolyl-alkyl thiolcarbamates. Not a single isoxazolyl-alkyl thiolcarbamate is described in these examples and, consequently, no indication is given regarding the herbicidal properties of these compounds and their selectivity with respect to crops.

SUMMARY OF THE INVENTION

The compounds according to the invention are of the following general formula:

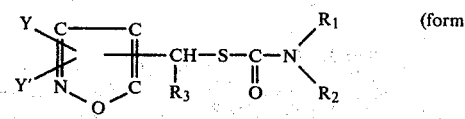

(formula A)

in which: $R_1$ and $R_2$ are identical or different and each represents a hydrogen atom, a linear or branched alkyl radical containing 1 to 6 carbon atoms, a cycloalkyl radical containing 3 to 6 carbon atoms, an alkenyl radical containing 2 to 4 carbon atoms, an alkoxy radical containing 1 to 6 carbon atoms, an alkoxyalkyl radical in which each alkyl part contains 1 to 4 carbon atoms, an optionally substituted aryl radical, an optionally substituted aralkyl radical in which the alkyl part contains 1 to 4 C, or a saturated or unsaturated heterocyclic radical which has 5 to 6 chain members and contains, as the hetero-atom an oxygen, nitrogen or sulphur atom, or $R_1$ and $R_2$ can also form, together with the nitrogen atom to which they are bonded, a saturated or unsaturated, optionally substituted heterocyclic structure which has 5 to 8 chain members and can contain, as a hetero-atom, an oxygen atom in addition to the nitrogen atom, $R_3$ represents a hydrogen atom or an alkyl radical containing 1 to 4 carbon atoms and Y and Y' are identical or different and each represents a hydrogen or halogen atom, an alkyl radical containing 1 to 6 carbon atoms, a trifluoromethyl radical or an optionally substituted aryl radical.

Herbicidal compositions of the invention, which can be used in agriculture, contain as the active material, at least one of the compounds defined by formula A.

DESCRIPTION OF THE INVENTION

Depending on the position of the alkyl thiolcarbamate radical of an isoxazole ring, the compounds according to the general formula A cited further above correspond to one or another of the formulae B, C and D which follow:

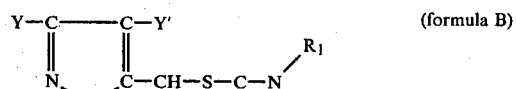

(formula B)

(formula C)

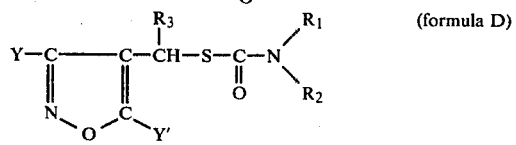

(formula D)

in which $R_1$, $R_2$, $R_3$, Y and Y' have the same meaning as in formula A.

The compounds according to the invention generally have an excellent herbicidal activity against graminaceous weeds, such as, for example, wild oats (*Avena fatua*), crabgrass (*Digitaria sanguinalis*), barnyard grass (*Echinochloa crus-galli*) raygrass (*Lolium multiflorum*), foxtail (*Setaria faberii*) and slender foxtail (*Alopecurus myosuroides*). Some of the compounds also have a good herbicidal action against dicotyledonous weeds, such as goosefoot (*Chenopodium album*), nightshade (*Solanum nigrum*), mustard (*Sinapis arvensis*) and chickweed (*Stellaria media*). They can be used for the selective destruction of weeds in crops such as maize, groundnuts, rape, cotton, soya, sunflowers, wheat, beans and rice and are applied before sowing or before emergence of the crops.

The compounds according to the general formula A are prepared according to a process which is analogous to that described in U.S. Pat. No. 3,579,525 for preparation of pyridylmethyl thiol- or dithiol-carbamates but which is used here for the preparation of isoxazolylalkyl thiolcarbamates, in accordance with the global reaction equation:

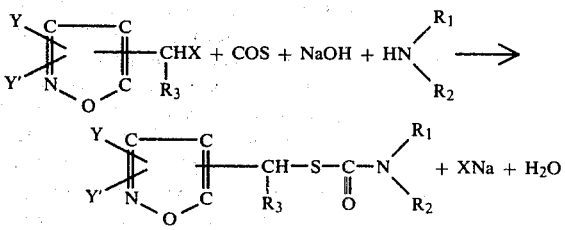

in which Y, Y′, R₁, R₂ and R₃ have the same meaning as in formula A and X represents a chlorine or bromine atom.

For this purpose, the amine HNR₁R₂ and carbon oxysulphide are reacted, in a first stage, in the presence of sodium hydroxide in an aqueous or aqueous-organic medium at a temperature of between 0° and 20° C. and preferably of about 10° C., in order to obtain a sodium thiolcarbamate, and the halogenoalkylisoxazole is then added to the reaction mixture, the reaction being carried out at a temperature of between 0° and 80° C. After stirring for a period of 1 to 4 hours, the reaction mixture is decanted and the aqueous phase is then extracted with a solvent, such as, for example, benzene. The organic phase thus obtained is then washed and dried and the solvent is removed by the usual procedures, for example by evaporation under reduced pressure.

Depending on whether the compound which it is desired to prepare falls under formula B, C or D given above, the starting material used is a halogenoalkyl-isoxazole of one of the following formulae:

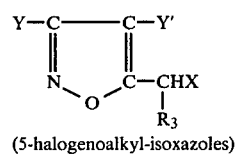

(5-halogenoalkyl-isoxazoles)    Formula B′

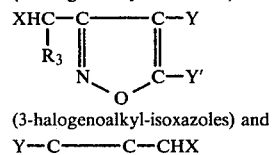

(3-halogenoalkyl-isoxazoles) and    Formula C′

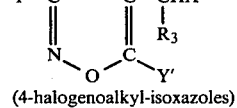

(4-halogenoalkyl-isoxazoles)    Formula D′ respectively, in which R₁,R₂, R₃, X, Y and Y′ have the same meaning as above.

The 5-halogenoalkyl-isoxazoles of the formula B′ can be prepared by several processes which are in themselves known.

According to a first process, the compounds according to the formula B′, in which X, Y and R₃ have the same meaning as above and Y′ represents a hydrogen atom or an alkyl, trifluoromethyl or optionally substituted aryl radical, are prepared by the cycloaddition of a nitrile oxide onto a halogenoalkyne, in accordance with the reaction equation:

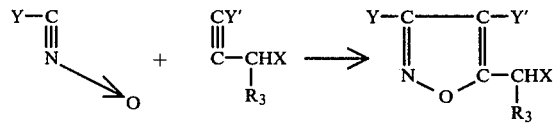

This process has been described in Atti Soc peloritana Sci fis mat nat 3,179–86 (1956-57) for the preparation of 3-phenyl-5-chloromethyl-isoxazole.

Because of the instability of the nitrile oxide, it is preferable to prepare this oxide in situ.

For this purpose, according to a first process which is in itself known, a nitroalkane of the formula Y—CH₂NO₂ is dehydrated by means of a phenyl isocyanate, in the presence of a tertiary amine, in accordance with the reaction equation:

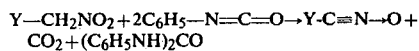

in which Y has the same meaning as above.

This process has been described in J Amer. Chem. Soc. 82 p. 5339 (1960) and also in Belgian Pat. No. 772,490 for the preparation of 3-alkyl-5-halogenomethyl-isoxazoles.

The nitrile oxide can also be prepared in situ according to a process which is in itself known by reacting a mineral or organic base with a chloroaldoxime, in accordance with the reaction equation:

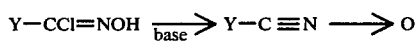

This process has been described in Atti Soc. peloritana Sci fis mat nat 3,179–86 (1956-57) for the preparation of 3-methyl-5-chloromethyl-isoxazole.

The chloroaldoxime can also be prepared in situ by reacting chlorine with an aldoxime at a temperature of between −20° C. and +5° C., either in an organic solvent medium, for example methylene chloride or petroleum ether, or in aqueous media, for example in a dilute aqueous solution of hydrochloric acid.

The 5-halogenoalkyl-isoxazoles of the formula

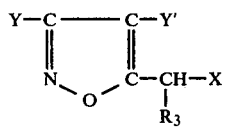

in which Y has the same meaning as above and Y′ represents a halogen atom, can be obtained directly by halogenation of compounds of the formula

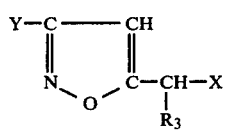

according to a method which is in itself known and is described in Rend ist lombardo sci 69, 587–601, 1936, for the preparation of 5-methyl-4-chloro-isoxazole and of 5-methyl-4-bromo-isoxazole.

The 3-halogenoalkyl-isoxazoles according to formula C′ can be prepared by the following processes:

According to a first process, which is in itself known, the compounds according to the formula C′, in which X and Y′ have the same meaning as above and Y represents a hydrogen atom or an alkyl, trifluoromethyl or optionally substituted aryl radical, can be prepared by reacting an acid chloride with an alkyne, and then treating the halogenoalkyl vinyl ketone thus obtained with a hydroxylamine hydrochloride, in accordance with the following reaction equation:

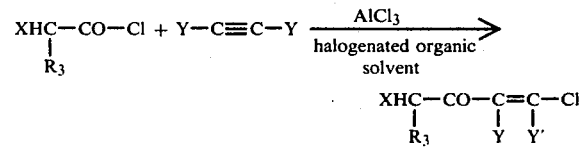

-continued

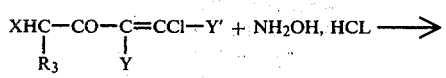

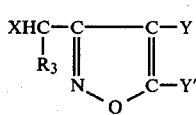

The compounds according to the formula C' in which Y is a halogen atom can be obtained by halogenation of compounds in which Y represents a hydrogen atom, in accordance with the method described by "Rend ist lombardo Sci" 69, 587–601, 1936, already cited above.

The 4-halogenoalkyl-isoxazoles of the formula D' can be prepared, according to a process which is in itself known and is described in Zhur Obshchei Khim 28 2736–45 (1958) for the preparation of 3-methyl-4-chloromethyl-isoxazole, 5-methyl-4-chloromethyl-isoxazole, 4-chloromethyl-isoxazole and 5-phenyl-4-chloromethyl-isoxazole.

According to this process, the 4-chloroalkyl-isoxazoles of the formula

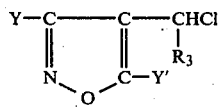

in which $R_3$, Y and Y' have the same meaning as above, are obtained by the action of paraformaldehyde and hydrochloric acid, in the presence of $ZnCl_2$, on an isoxazole of the formula

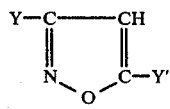

The 4-bromoalkyl-isoxazoles and 4-iodoalkyl-isoxazoles can be obtained using the 4-chloroalkyl-isoxazoles as the starting materials, in accordance with the process described in Isvest Akad Nauk SSSR Otdel Khim Nauk 1952 87–92.

The examples which follow illustrate the invention without, however, restricting it.

In the text which follows, Example B'$_1$ to B'$_6$, C'$_1$ to C'$_2$ and D'$_1$ relate, respectively, to the preparation of halogenoalkyl-isoxazoles of the general formulae B', C' and D' respectively and Examples 1 to 4 relate to the preparation of isoxazolyl-alkyl thiolcarbamates according to the invention and to the tests showing the herbicidal activity of these compounds.

Preparation of halogenoalkyl-isoxazoles

EXAMPLE B'1

Preparation of 3-methyl-5-chloromethyl-isoxazole using nitroethane as the starting material 238.0 g (2 mols) of phenyl isocyanate and 82.0 g (1.1 mols) of 3-chloro-propyne in 500 ml of benzene are brought to a temperature of 85° C. A solution of 75.0 g (1 ml) of nitroethane and 10 ml of triethylamine in 250 ml of benzene is then run in dropwise. After a few minutes, a precipitate of urea appears and carbon dioxide gas is evolved. The addition is made at a rate which is just sufficient to maintain boiling without external heating. Reflux is maintained by heating for one hour after the end of the addition. After cooling, the mixture is filtered, the filtrate is concentrated and the residue is distilled under reduced pressure. This gives: 97.0 g of 3-methyl-5-chloromethyl-isoxazole.

Boiling point: 80° C./15 mm Hg. Yield: 73.7%.

EXAMPLE B'2

The following compounds were prepared from suitable starting materials using a procedure as in Example B'1:

3-methyl-5-bromomethyl-isoxazole; boiling point 50° C. (0.5 mm Hg)

3-ethyl-5-chloromethyl-isoxazole; boiling point 90° C. (13 mm Hg), $n_D^{20}=1.454$, and 3-methyl-5-(1-chloroethyl)-isoxazole; boiling point 82° C. (14 mm Hg), $n_D^{25}=1.4755$.

EXAMPLE B'3

Preparation of 3-(tertiary butyl)-5-chloromethyl-isoxazole, using pivaldoxime as the starting material 37.8 g (0.37 mol) of pivaldoxime dissolved in 400 ml of methylene chloride are chlorinated with 26.5 g (0.37 mol) of chlorine at a temperature of between −5° C. and 0° C. After stirring for +minutes at 0° C., 28 g (0.37 mol) of 3-chloro-propyne are added and 30 g (0.75 mol) of sodium hydroxide dissolved in 200 ml of water are run in, whilst stirring vigorously, at a temperature of about 5° C. Stirring is continued overnight, the temperature being allowed to rise to ambient temperature.

The mixture is decanted and the aqueous phase is extracted with methylene chloride. The combined organic phases are dried and the solvent is evaporated. The residue is distilled under reduced pressure and this gives: 56.2 g of 3-(tertiary butyl)-5-chloromethyl-isoxazole.

yield=85.5%. Boiling point: 80° C./15 mm Hg.

EXAMPLE B'4

The following compounds were prepared from suitable starting materials using a procedure as in Example B'3.

3-methyl-5-chloromethyl-isoxazole; boiling point 86°–89° C. (19 mm Hg), $n_D^{25}=1.4797$ 3-(n-proply)-5-chloromethyl-isoxazole; boiling point: 110°–112° C. (14 mm Hg), $n_D^{25}=1,4744$ 3-isopropyl-5-chloromethyl-isoxazole; boiling point= 100°–106° C. (15 mm Hg), $n_D^{20}=1.4707$ 3-isopropyl-5-(1-chloroethyl)-isoxazole; boiling point: 102°–106° C. (14 mm Hg)

3-phenyl-5-chloromethyl-isoxazole; melting point: 69.2° C., and 3-(2,6-dichlorophenyl)-5-chloromethyl-isoxazole; boiling point: 148°–149° C. (0.05 mm Hg), $n_D^{20}=1.5883$

EXAMPLE B'5

Preparation of 3-methyl-4-chloro-5-(1-chloroethyl)-isoxazole by chlorination of 3-methyl-5(1-chloroethyl)-isoxazole 29.1 g (0.2 mol) of 3-methyl-5-(1-chloroethyl)-isoxazole are run dropwise into 54.0 g (0.4 mol) of sulphuryl chloride at abient temperature. The reaction mixture is left to stand for 48 hours at ambient temperature and is then concentrated and distilled under reduced pressure. This gives: 31.0 g of 3-methyl-4-chloro-5-(1-chloroethyl)-isoxazole; boiling point=89°–91° C./17 mm Hg.

Yield: 86.1%.

EXAMPLE B'6 the following products were prepared from suitable starting materials using a procedure as in Example B'5:
3-methyl-4-chloro-5-chloromethyl-isoxazole; boiling point 83°–84° C./15 mm Hg, $n_D^{25} = 1.4935$
3-methyl-4-bromo-5-bromomethyl-isoxoazole; boiling point 90°–93° C./11 mm Hg, melting point: 38° C.
3-ethyl-4-chloro-5-chloromethyl-isoxazole; boiling point: 97°–100° C./17 mm Hg, $n_D^{25}:1.4905$, and
3-isopropyl-4-chloro-5-(1-chloroethyl)-isoxazole; $n_D^{25}:1.4786$

EXAMPLE C'1

113 g (1 mol) of monochloroacetyl chloride are run dropwise into a suspension of 180 g of aluminum chloride in 400 ml of anhydrous ethylene chloride at a temperature below 5° C. A stream of acetylene is then passed in, whilst keeping the temperature at between 0° and 10° C., for 3 hours 30 minutes.

The reaction mixture is then poured onto 1 kg of ice and 20 ml of concentrated hydrochloric acid. After stirring for 30 minutes, the mixture is decanted and the aqueous phase is extracted with twice 100 ml of methylene choride. The organic phases are washed successively with water, with a bicarbonate solution and finally with water, and dried over MgSO₄ after evaporation of the solvents. The residue is distilled under reduced pressure. This gives 106.1 g of chloromethyl 2-chlorovinyl ketone (90% trans isomer and 10% cis isomer); yield: 76.3%. Boiling point: 74°–79° C./18 mm Hg.

60.0 g (0.43 mol) of chloromethyl chlorovinyl ketone and 30.0 g (0.43 mol) of hydroxylamine hydroxylamine dissolved in 300 ml of methanol are heated under reflux for 3 hours. The methanol is then distilled under atmospheric pressure and the residue is taken up in 150 ml of methylene chloride. The aqueous phase which separates out is decanted off and extracted with methylene chloride. After drying over magnesium sulphate and evaporating off the solvent, the residue is distilled under reduced pressure. This gives 40.9 g (yield: 80.7%) of 3-chloromethyl-isoxazole; boiling point: 63°–66° C./19 mm Hg.

EXAMPLE C'2

The following compounds were prepared from suitable starting materials using a procedure as indicated in Example C'1;
3-(1-chloroethyl)-isoxazole; boiling point: 67°–68°/21 mm Hg, $n_D^{25}:1.4685$
3-chloromethyl-5-methyl-isoxazole and
3-(1-chloroethyl)-5-methyl-isoxazole.

EXAMPLE D'1

4-Chloromethyl-3,5-dimethyl-isoxazole was obtained according to the preparation described in Zhur Obshchei Khim 28 2736-45 1958; boiling point: 90°–95° C. under 16 mm Hg.

Preparation of isoxazolyl-alkyl thiolcarbamtes according to the invention

EXAMPLE 1

Preparation of 3-methyl-isoxazol-5-yl-methyl N,N-di-(n-propyl)-thiolcarbamate (compound No. 3).

115.2 g (2.88 mols) of sodium hydroxide pellets and 290.9 g (2.88 mols) of di-n-propylamine are dissolved in 2.5 l of water and the solution is cooled to 10° C. using a bath of ice-water. 172.8 g (2.88 mols) of carbon oxysulphide are absorbed into this solution with the aid of a finger-shaped glass frit, any gas which may not have been absorbed being condensed in a condenser cooled by a mixture of solid carbon dioxide/acetone. The reaction mixture is then stirred for 10 minutes at 10° C. and 315.6 g (2.4 mols) of 3-methyl-5-chloromethyl-isoxazole are then added rapidly. The mixture is stirred for 3 hours, the temperature being allowed to rise to ambient temperature, and then decanted and the aqueous phase is extracted with twice 500 ml of benzene and the combined organic phases are then washed with water until neutral, dried over magnesium sulphate, concentrated and distilled under reduced pressure. This gives 526.6 g of 3-methyl-isoxazol-5-yl-methyl N,N-di-(n-propyl)-thiolcarbamate. Boiling point=137° C./0.06 mm Hg. Yield: 85.7%. $n_D^{25} = 1.5091$.

The preparation of 3-methyl-5-chloromethyl-isoxazole which is used as the starting material has been describe in Example B'1.

EXAMPLE 2

Preparation of 3-methyl-isoxazol-5-yl-methyl N,N-diiso-propyl-thiolcarbamate (compound No. 10)

120 g (3 mols) of sodium hydroxide and 303 g (3 mols) of diisopropylamine are dissolved in 1.5 l of water and the solution is cooled to about 10° C. 135 g (2.25 mols) of carbon oxysulphide are absorbed by this solution, wit the aid of a finger-shaped glass frit, the gas which has not been absorbed being condensed in a condenser containing solid carbon dioxide/acetone.

After the reaction mixture has been stirred for 10 minutes at 10° C., 197.2 g (1.5 mols) of 3-methyl-5-chloromethyl-isoxazole are added rapidly, whilst stirring vigorously. A white precipitate forms immediately. Stirring is continued for 4 hours, the temperature being allowed to rise to ambient temperature. The precipitate is then filtered off and washed with water until neutral and is then dried at 40° C. under reduced pressure. This gives 353.5 g of 3-methyl-isoxazol-5-yl-methyl N,N-diisopropyl-thiolcarbamate.

Melting point=67°–68° C.; yield: 92%.

The preparation of 3-methyl-5-chloromethyl-isoxazole, which is the starting material, has been described in Example B'1.

EXAMPLE 3

Following the procedure of Example 1, compounds 1, 2, 4 to 9 and 11 to 70 were prepared starting from suitable starting materials. The physico-chemical characteristics of these compounds are given in the table below.

In this table:
the defining the alkyl radicals have the following meanings:
Me: methyl
Et: ethyl
Pr: normal propyl
iso Pr: isopropyl
Bu: primary normal butyl
sec. Bu: secondary normal butyl
iso-Bu: isobutyl
ter-Bu: tertiary butyl
and the symbol (B), (C) or (D) given below the number of each compound indicates to which of the formulae B, C and D this compound corresponds.

(Formula B)

| Compound No. | $R_1$ | $R_2$ | $R_3$ | Y | Y' | Empirical formula | Molecular weight | Physical constants | Yield | | Elementary Analysis | | | |
|---|---|---|---|---|---|---|---|---|---|---|---|---|---|---|
| | | | | | | | | | | | C | H | N | S |
| 1 (B) | Me | Me | H | Me | H | $C_8H_{12}N_2O_2S$ | 200 | boiling point: 112° C./ 0.008 mm Hg melting point: 33–34° C. | 68.5% | calculated: found: | 48.00 48.09 | 6.00 6.07 | 14.00 14.14 | 16.00 15.98 |
| 2 (B) | Et | Et | H | Me | H | $C_{10}H_{16}N_2O_2S$ | 228 | boiling point: 117° C./ 0.02 mm Hg melting point: 38–39° C. | 55.8% | calculated: found: | 52.63 52.50 | 7.02 6.97 | 12.88 12.42 | 14.09 14.21 |
| 3 (B) | Pr | Pr | H | Me | H | $C_{12}H_{20}N_2O_2S$ | 256 | boiling point: 137° C./ 0.06 mm Hg $n_D^{25}$ : 1.5091 | 85.7% | calculated: found: | 56.23 56.21 | 7.87 7.91 | 10.93 10.92 | |
| 4 (B) | Bu | Bu | H | Me | H | $C_{14}H_{24}N_2O_2S$ | 284 | boiling point: 104° C. molecular distillation $n_D^{25}$ : 1.5047 | 70.4% | calculated: found: | 59.15 59.09 | 8.45 8.42 | 9.86 9.37 | 11.27 11.36 |
| 5 (B) | Me | Pr | H | Me | H | $C_{10}H_{16}N_2O_2S$ | 228 | boiling point: 132° C./ 0.06 mm Hg $n_D^{25}$ = 1.5185 | 77.3% | calculated: found: | 52.63 51.16 | 7.02 7.14 | 12.23 12.29 | |
| 6 (B) | Me | iso Pr | H | Me | H | $C_{10}H_{16}N_2O_2S$ | 228 | boiling point: 116–113° C. 0.05 mm Hg $n_D^{25}$ : 1.5203 | 58.5% | calculated: found: | 52.63 51.66 | 7.02 7.07 | 12.28 12.26 | |
| 7 (B) | Me | Bu | H | Me | H | $C_{11}H_{18}N_2O_2S$ | 242 | boiling point: 128° C./ 0.075 mm Hg $n_D^{25}$ : 1.5142 | 75.9% | calculated: found: | 54.54 53.21 | 7.44 7.71 | 11.57 11.27 | |
| 8 (B) | Me | sec Bu | H | Me | H | $C_{11}H_{18}N_2O_2S$ | 242 | boiling point: 129° C./ 0.065 mm Hg $n_{25}^D$ : 1.5153 | 80.7% | calculated: found: | 54.54 53.47 | 7.44 7.63 | 11.57 11.34 | |
| 9 (B) | Et | Bu | H | Me | H | $C_{12}H_{20}N_2O_2S$ | 256 | boiling point: 112–118° C. | 65.3% | calculated: found: | 56.25 55.26 | 7.81 7.87 | 10.94 11.03 | |

-continued
(Formula B)

| Compound No. | R₁ | R₂ | R₃ | Y | Y' | Empirical formula | Molecular weight | Physical constants | Yield | | Elementary Analysis | | | |
|---|---|---|---|---|---|---|---|---|---|---|---|---|---|---|
| | | | | | | | | | | | C | H | N | S |
| 10 (B) | iso P | iso Pr | H | Me | H | C₁₂H₂₀N₂O₂S | 256 | 0.06 mm Hg $n_D^{25}$ : 1.5097 melting point: 67–68° C. | 92% of crude product 84.5% | calculated: found: | 56.22 56.08 | 7.86 7.92 | 10.93 10.93 | 12.50 12.49 |
| 11 (B) | iso Bu | iso Bu | H | Me | H | C₁₄H₂₄N₂O₂S | 284 | boiling point: 114–119° C. 0.055 mm Hg $n_D^{25}$ : 1.5020 | 68.9% | calculated: found: | 59.15 59.41 | 8.45 8.56 | 9.86 9.86 | |
| 12 (B) | Et | Et | H | Et | H | C₁₁H₁₈N₂O₂S | 242 | boiling point: 120° C./ 0.02 mm Hg $n_D^{25}$ : 1.5134 | 59.2% | calculated: found: | 54.55 54.59 | 7.44 7.47 | 11.57 11.51 | 13.22 13.30 |
| 13 (B) | Pr | Pr | H | Et | H | C₁₃H₂₂N₂O₂S | 270 | boiling point: 120° C./ 0.013 mm Hg $n_D^{25}$ : 1.5066 | 79.2% | calculated: found: | 57.78 58.04 | 8.15 7.88 | 10.37 10.35 | 11.85 11.98 |
| 14 (B) | iso Pr | iso Pr | H | Et | H | C₁₃H₂₂N₂O₂S | 270 | boiling point: 120° C./ 0.06 mm Hg $n_D^{25}$ : 1.5081 | 85.8% | calculated: found: | 57.78 57.86 | 8.15 8.28 | 10.37 10.41 | |
| 15 (B) | Pr | Pr | H | Pr | H | C₁₄H₂₄N₂O₂S | 284 | boiling point: 130° C./ 0.06 mm Hg $n_D^{25}$ : 1.5038 | 62% | calculated: found: | 59.15 59.08 | 8.45 8.56 | 9.86 9.89 | 11.27 11.38 |
| 16 (B) | iso Pr | iso Pr | H | Pr | H | C₁₄H₂₄N₂O₂S | 284 | boiling point: 121° C./ 0.001 mm Hg $n_D^{25}$ : 1.5090 | 38.3% | calculated: found: | 59.15 59.37 | 8.45 8.50 | 9.86 10.06 | |
| 17 (B) | Et | Et | H | iso Pr | H | C₁₂H₂₀N₂O₂S | 256 | boiling point: 129–132° C./ $n_D^{25}$ : 1.5028 | 50.6% | calculated: found: | 56.25 56.24 | 7.81 7.88 | 10.94 10.88 | 12.50 12.57 |
| 18 (B) | Pr | Pr | H | iso Pr | H | C₁₄H₂₄N₂O₂S | 284 | boiling point: 123° C./ 0.06 mm Hg $n_D^{25}$ : 1.5030 | 66.5% | calculated: found: | 59.15 59.16 | 8.45 8.55 | 9.86 10.01 | 11.27 11.29 |
| 19 (B) | iso Pr | iso Pr | H | iso Pr | H | C₁₄H₂₄N₂O₂S | 284 | | | calculated: found: | 59.15 59.10 | 8.45 8.48 | 9.86 9.92 | |
| 20 | Pr | Pr | H | ter | H | C₁₅H₂₆N₂O₂S | 298 | $n_D^{25}$ : 1.5013 | 90% | calcu- | | | | |

-continued
(Formula B)

| Compound No. | $R_1$ | $R_2$ | $R_3$ | Y | Y' | Empirical formula | Molecular weight | Physical constants | Yield | | Elementary Analysis | | | |
|---|---|---|---|---|---|---|---|---|---|---|---|---|---|---|
| | | | | | | | | | | | C | H | N | S |
| 21 (B) | iso Pr | iso Pr | H | Bu | H | $C_{15}H_{26}N_2O_2S$ | 298 | boiling point: 122° C./ 0.06 mm Hg $n_{25}^D$: 1.5003 | 75.8% | calculated: found: | 60.40 60.46 | 8.72 8.60 | 9.40 9.39 | 10.74 10.68 |
| 22 (B) | Pr | Pr | H | ter Bu | H | $C_{17}H_{22}N_2O_2S$ | 318 | $n_{25}^D$: 1.5663 | 86.7% | calculated: found: | 60.40 60.36 | 8.72 8.68 | 9.40 9.91 | |
| 23 (B) | Et | Et | H | Ph | H | $C_{17}H_{22}N_2O_2S$ | 318 | $n_{25}^D$ = 1.5885 | 87.4% | calculated: found: | 64.15 64.16 | 6.92 6.86 | 8.80 8.95 | 10.06 9.99 |
| 24 (B) | Pr | Pr | H | 2,6-diCl-Me-Ph | H | $C_{17}H_{20}Cl_2N_2O_2S$ | 387 | $n_{25}^D$: 1.5706 | 90% | calculated: found: | 50.14 49.94 | 4.45 4.44 | 7.80 7.76 | 8.91 8.81 |
| 25 (B) | Et | Et | Me | Me | H | $C_{11}H_{18}N_2O_2S$ | 242 | boiling point: 118° C./ 0.015 mm Hg $n_{25}^D$: 1.5137 | 56.2% | calculated: found: | 52.71 52.66 | 5.17 5.14 | 7.23 6.85 | 8.27 7.90 |
| 26 (B) | Pr | Pr | Me | Me | H | $C_{13}H_{22}N_2O_2S$ | 270 | boiling point: 120° C./ 0.001 mm Hg $n_{25}^D$: 1.5070 | 30.6% | calculated: found: | 54.50 54.60 | 7.44 7.46 | 11.57 11.48 | 13.22 13.16 |
| 27 (B) | Pr | Pr | Me | iso Pr | H | $C_{15}H_{26}N_2O_2S$ | 298 | boiling point: 134-137° C. 0.003 mm Hg $n_{25}^D$: 1.5040 | 57.7% | calculated: found: | 57.78 57.97 | 8.15 7.91 | 10.37 10.46 | 11.85 12.01 |
| 28 (B) | Et | Et | H | Me | Cl | $C_{10}H_{15}ClN_2O_2S$ | 262.5 | boiling point: 126° C./ 0.06 mm Hg $n_{25}^D$: 1.5245 | 66.9% | calculated: found: | 60.40 58.70 | 8.72 8.39 | 9.39 8.65 | |
| 29 (B) | Pr | Pr | H | Me | Cl | $C_{12}H_{19}ClN_2O_2S$ | 290.5 | boiling point: 128° C./ 0.045 mm Hg $n_{25}^D$: 1.5154 | 81.6% | calculated: found: | 45.71 45.68 | 5.71 5.63 | 10.67 10.59 | 12.15 12.31 |
| 30 (B) | Pr | Pr | H | Me | Br | $C_{12}H_{19}BrN_2O_2S$ | 335 | $n_{25}^D$: 1.5298 | 70% | calculated: found: | 49.57 49.73 | 6.54 6.56 | 9.64 9.63 | 11.01 10.96 |
| 31 | Et | Et | H | Et | Cl | $C_{11}H_{17}ClN_2O_2S$ | 276.5 | boiling point: | 81.8% | calculated: | 42.98 43.07 | 5.67 5.70 | 8.36 8.32 | 9.55 9.60 |

-continued
(Formula B)

| Compound No. | R₁ | R₂ | R₃ | Y | Y' | Empirical formula | Molecular weight | Physical constants | Yield | | Elementary Analysis | | | |
|---|---|---|---|---|---|---|---|---|---|---|---|---|---|---|
| | | | | | | | | | | | C | H | N | S |
| 31 (B) | Pr | Pr | H | Et | Cl | $C_{13}H_{21}ClN_2O_2S$ | 304.5 | 120–123° C. 0.02 mm Hg $n_{25}^D$: 1.5196 | 97.2% | calculated: found: | 47.74 47.70 | 6.15 6.19 | 10.13 10.07 | 11.57 11.60 |
| 32 (B) | Me | Me | Me | Me | Cl | $C_9H_{13}ClN_2O_2S$ | 248.5 | boiling point: 106–109° C. 0.03 mm Hg $n_{25}^D$: 1.5146 | 35.8% | calculated: found: | 51.23 51.12 | 6.90 7.05 | 9.19 9.18 | 10.51 10.60 |
| 33 (B) | Me | Me | Me | Me | Cl | $C_{11}H_{17}ClN_2O_2S$ | 276.5 | boiling point: 114–119° C. 0.03 mm Hg $n_{25}^D$: 1.5273 | 44% | calculated: found: | 43.46 43.70 | 5.23 5.04 | 11.27 11.40 | 12.88 12.89 |
| 34 (B) | Et | Et | Me | Me | Cl | $C_{13}H_{21}ClN_2O_2S$ | 304.5 | boiling point: 122–12° C. 0.016 mm Hg $n_{25}^D$: 1.5214 | 47.5% | calculated: found: | 47.74 47.73 | 6.15 6.12 | 10.13 9.98 | 11.57 11.56 |
| 35 (B) | Pr | Pr | Me | Me | Cl | $C_{12}H_{16}N_2O_2S$ | 252 | boiling point: 124° C./ 0.011 mm Hg $n_{25}^D$: 1.5128 | 71.2% | calculated: found: | 51.23 50.94 | 6.90 7.14 | 9.19 9.07 | 10.51 10.56 |
| 36 (B) | —CH₂—CH=CH₂ | —CH₂—CH=CH₂ | H | Me | H | $C_{12}H_{16}N_2O_2S$ | 252 | boiling point: 124° C./ 0.011 mm Hg $n_{25}^D$: 1.5306 | 71.2% | calculated: found: | 57.14 56.94 | 6.35 6.24 | 11.11 11.17 | 12.70 12.85 |
| 37 (B) | —CH₂—CH=CH₂ | —CH₂—CH=CH₂ | H | iso Pr | H | $C_{14}H_{20}N_2O_2S$ | 280 | boiling point: 132° C. 0.04 mm Hg $n_{25}^D$: 1.5210 | 54.7% | calculated: found: | 60.00 59.85 | 7.14 7.09 | 10.00 10.09 | 11.43 11.56 |
| 38 (B) | —CH₂—CH=CH₂ | —CH₂—CH=CH₂ | Me | Me | H | $C_{13}H_{18}N_2O_2S$ | 266 | boiling point: 123–125 0.035 mm Hg $n_{25}^D$: 1.5273 | 46.7% | calculated: found: | 58.65 58.73 | 6.77 6.39 | 10.53 10.60 | 12.03 12.17 |
| 39 (B) | —CH₂—CH=CH₂ | —CH₂—CH=CH₂ | H | Et | Cl | $C_{13}H_{17}ClN_2O_2S$ | 300.5 | $n_{25}^D$: 1.5320 | 88.8% | calculated: found: | 51.91 52.32 | 5.66 5.79 | 9.32 9.43 | 10.65 10.80 |
| 40 (B) | —CH₂—CH=CH₂ | —CH₂—CH=CH₂ | Me | Me | Cl | $C_{13}H_{17}ClN_2O_2S$ | 300.5 | boiling point: 123–127° C./ 0.025 mm Hg $n_{25}^D$: 1.5295 | 47.2% | calculated: found: | 51.91 51.90 | 5.66 5.68 | 9.32 9.37 | 10.65 10.68 |
| 41 (B) | H | 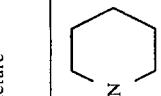 | H | Me | H | $C_{12}H_{12}N_2O_2S$ | 248 | melting point: 95° C. | 38.3% | calculated: found: | 58.06 58.14 | 4.84 4.89 | 11.29 11.23 | 12.90 12.84 |
| 42 (B) | heterocyclic structure formed by N, R₁ and R₂ | | H | Me | H | $C_{11}H_{16}N_2O_2S$ | 240 | melting point: 92.3° C. | 92.3% | calculated: | 55.00 | 6.67 | 11.67 | 13.33 |

-continued
(Formula B)

| Compound No. | R₁ | R₂ | R₃ | Y | Y' | Empirical formula | Molecular weight | Physical constants | Yield | | Elementary Analysis | | | |
|---|---|---|---|---|---|---|---|---|---|---|---|---|---|---|
| | | | | | | | | | | | C | H | N | S |
| 43 (B) | | (azepane) | H | Me | H | $C_{12}H_{18}N_2O_2S$ | 254 | boiling point: 160° C./ 0.05 mm Hg $n_{25}^D$: 1.5420 | 67.1% | calculated: found: | 56.69 56.64 | 7.09 7.06 | 11.02 11.06 | 12.60 12.65 |
| 44 (B) | | (azepane) | H | Et | H | $C_{13}H_{20}N_2O_2S$ | 268 | boiling point: 140° C./ 0.016 mm Hg $n_{25}^D$: 1.5368 | 62.8% | calculated: found: | 58.21 58.18 | 7.46 7.47 | 10.45 10.39 | 11.94 11.94 |
| 45 (B) | | (morpholine) | H | Me | H | $C_{10}H_{14}N_2O_3S$ | 242 | boiling point: 150° C./ 0.01 mm Hg melting point: 61.5 | 30.7% | calculated: found: | 49.59 49.59 | 5.78 5.61 | 11.57 11.60 | 13.22 13.19 |

| No. | $R_1$ | $R_2$ | $R_3$ | Y | Y' | Empirical formula | Molecular weight | (Formula C) Physical constants | Yield | | Elementary analysis | | | |
|---|---|---|---|---|---|---|---|---|---|---|---|---|---|---|
| | | | | | | | | | | | C | H | N | S |
| 46 (C) | Et | Et | H | H | H | $C_9H_{14}N_2O_2S$ | 214 | $n_{25}^D$: 1.5190 | 91% | calculated: found: | 50.47 49.89 | 6.54 6.63 | 13.08 12.75 | |
| | | | | | | | | | | | C | H | N | S |
| 47 (C) | Pr | Pr | H | H | H | $C_{11}H_{18}N_2O_2S$ | 242 | $n_{25}^D$: 1.5147 | 83.4% | calculated: found: | 54.54 54.39 | 7.44 7.39 | 11.57 11.43 | 13.22 13.39 |
| | | | | | | | | | | | C | H | N | |
| 48 (C) | Bu | Bu | H | H | H | $C_{13}H_{22}N_2O_2S$ | 270 | $n_{25}^D$: 1.5048 | 99% | calculated: found: | 57.78 57.58 | 8.15 8.07 | 10.37 10.23 | |
| 49 (C) | iso Bu | iso Bu | H | H | H | $C_{13}H_{22}N_2O_2S$ | 270 | $n_{25}^D$: 1.5030 | 96.3% | calculated: found: | 57.78 56.56 | 8.15 8.18 | 10.37 10.22 | |
| 50 (C) | Et | Bu | H | H | H | $C_{11}H_{18}N_2O_2S$ | 242 | $n_{25}^D$: 1.5117 | 97.9% | calculated: found: | 54.54 53.48 | 7.44 7.45 | 11.57 11.41 | |
| 51 (C) | iso Pr | iso Pr | H | H | H | $C_{11}H_{18}N_2O_2S$ | 242 | $n_{20}^D$: 1.5130 | 84.5% | calculated: found: | 54.34 53.83 | 7.44 8.08 | 11.57 11.54 | |
| 52 (C) | Et | Et | Me | H | H | $C_{10}H_{16}N_2O_2S$ | 228 | $n_{25}^D$: 1.5120 | 33.9% | calculated: found: | 52.63 51.42 | 7.02 7.02 | 12.28 11.91 | |
| 53 (C) | Pr | Pr | Me | H | H | $C_{12}H_{20}N_2O_2S$ | 256 | $n_{25}^D$: 1.5183 | 30% | calculated: found: | 56.25 55.34 | 7.81 7.84 | 10.94 10.96 | |
| 54 (C) | iso Bu | iso Bu | Me | H | H | $C_{14}H_{24}N_2O_2$ | 284 | boiling point: 100–109° C./ 0.015 mm Hg $n_{25}^D$: 1.5075 | 37.3% | calculated: found: | 59.15 57.45 | 8.45 8.13 | 9.86 9.72 | |
| 55 (C) | Et | Et | H | H | Me | $C_{10}H_{16}N_2O_2S$ | 228 | $n_{25}^D$: 1.5165 | 96.8% | calculated: found: | 52.63 52.12 | 7.02 7.25 | 12.28 12.05 | |
| 56 (C) | Pr | Pr | H | H | Me | $C_{12}H_{20}N_2O_2S$ | 256 | $n_{25}^D$: 1.5105 | 98% | calculated: found: | 56.25 56.36 | 7.81 7.98 | 10.94 10.78 | |
| 57 (C) | Bu | Bu | H | H | Me | $C_{14}H_{24}N_2O_2S$ | 284 | $n_{25}^D$: 1.5041 | 98.5% | calculated: found: | 59.15 58.00 | 8.45 8.40 | 9.86 9.70 | |
| 58 C | Et | Bu | H | H | Me | $C_{12}H_{20}N_2O_2S$ | 256 | $n_{25}^D$: 1.5103 | 98% | calculated: found: | 56.25 55.64 | 7.81 7.82 | 10.94 10.94 | |
| 59 (C) | iso Pr | iso Pr | H | H | Me | $C_{12}H_{20}N_2O_2S$ | 256 | | 75.8% | calculated: found: | 56.25 54.80 | 7.81 7.76 | 10.94 10.92 | |
| 60 (C) | iso Bu | iso Bu | H | H | Me | $C_{14}H_{24}N_2O_2S$ | 284 | $n_{25}^D$: 1.5017 | 74% | calculated: found: | 59.15 58.02 | 8.45 8.30 | 9.86 9.70 | |
| | | | | | | | | | | | C | H | N | S |
| 61 (C) | iso Pr | iso Bu | H | H | H | $C_{12}H_{20}N_2O_2S$ | 256 | $n_D^{20}$: 1.510 | 87% | calculated: found: | 56.22 56.14 | 7.86 7.77 | 10.93 11.12 | 12.51 12.45 |
| 62 (C) | Pr | sec Bu | H | H | H | $C_{12}H_{20}N_2O_2S$ | 256 | $n_D^{20}$ = 1.510 | 85% | calculated: found: | 56.22 56.29 | 7.86 7.74 | 10.93 11.03 | 12.51 12.75 |
| 63 C | Et | iso Pr | H | H | H | $C_{10}H_{16}N_2O_2S$ | 228 | $n_D^{20}$ = 1.516 | 44% | calculated: found: | 52.61 52.32 | 7.06 7.01 | 12.27 12.10 | 14.04 14.22 |
| 64 (C) | Et | —⟨H⟩ | H | H | H | $C_{13}H_{20}N_2O_2S$ | 268 | $n_D^{20}$ = 1.534 | 90% | calculated: found: | 58.18 58.20 | 7.51 7.50 | 10.44 10.29 | 11.95 11.97 |
| 65 (C) | Me | —CH₂—CH₂—O—CH₃ | H | H | H | $C_9H_{14}N_2O_3S$ | 230 | $n_D^{20}$ = 1.521 | 68% | calculated: found: | 46.94 46.55 | 6.13 6.09 | 12.16 12.09 | 13.92 14.17 |
| | | | | | | | | | | | C | H | N | S |
| 66 (C) | Et | iso Bu | H | H | H | $C_{11}H_{18}N_2O_2S$ | 242 | $n_D^{20}$ = 1.510 | 87% | calculated: found: | 54.52 54.61 | 7.49 7.52 | 11.56 11.47 | 13.23 13.13 |
| 67 (C) | Me | iso Bu | H | H | H | $C_{10}H_{16}N_2O_2S$ | 228 | $n_D^{20}$ = 1.515 | 74% | calculated: found: | 52.61 52.61 | 7.06 6.99 | 12.27 11.98 | 14.04 14.05 |
| | | | | | | | | | | | C | H | N | |
| 68 | iso | iso | H | H | H | $C_{11}H_{18}N_2O_2S$ | 242 | $n_D^{20}$ = 1.513 | 84.5% | calcu- | | | | |

-continued

| | | | | | | (Formula C) | | | | |
|---|---|---|---|---|---|---|---|---|---|---|
| No. | $R_1$ | $R_2$ | $R_3$ | Y | Y' | Empirical formula | Molecular weight | Physical constants | Yield | Elementary analysis |
| (C) | Pr | Pr | | | | | | | lated:<br>found: | 54.54 7.44 11.57<br>53.83 8.08 11.54 |

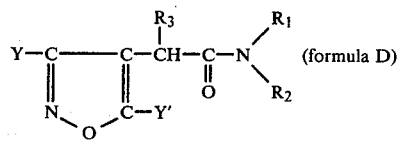

| No. | $R_1$ | $R_2$ | $R_3$ | Y | Y' | Empirical formula | Molecular weight | Physical constants | Yield | Percentage analysis | | | |
|---|---|---|---|---|---|---|---|---|---|---|---|---|---|
| 69 (D) | Pr | Pr | H | Me | H | $C_{13}H_{22}N_2O_2S$ | 270 | $n_{25}^D = 1.5094$ | 87% | | C | H | N | S |
| | | | | | | | | | | calculated:<br>found: | 57.78<br>57.96 | 8.15<br>7.96 | 10.37<br>10.48 | 11.85<br>11.98 |

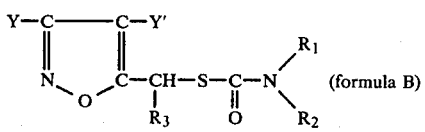

| 70 (B) | iso Pr | iso Bu | H | Me | H | $C_{13}H_{22}N_2O_2S$ | 270 | $n_{20}^D : 1.509$ | 83.5% | | C | H | N | S |
|---|---|---|---|---|---|---|---|---|---|---|---|---|---|---|
| | | | | | | | | | | calculated:<br>found: | 57.75<br>57.68 | 8.20<br>8.18 | 10.36<br>10.42 | 11.86<br>11.69 |

EXAMPLE 4

Herbicidal activity in the pre-emergence treatment of crops in a greenhouse.

A number of seeds chosen in accordance with the plant species and the size of the seed is sown in 9×9×9 ml pots filled with light agricultural soil.

The seeds are then covered with a layer of soil about 3 mm thick.

After moistening the soil, the pots are treated by spraying with an amount of liquor per pot which corresponds to a volume of 500 l/ha and contains the active material in the dose in question.

The liquor is prepared by diluting, with water, an emulsifiable concentrate having the following composition by weight:
active material to be tested: 20%
wetting and deflocculating agent: 10%
cyclohexanone (sovent): 70%
to the desired dilution, containing the active material in the dose in question. The tests were carried out at doeses of active material ranging from 1 kg/ha to 8 kg/ha.

The treated pots are then placed in troughs intended to receive the watering water by sub-irrigation, and are kept for 35 days at ambient temperature under 70% relative humidity.

After 35 days, the degree of destruction is determined relative to a reference sample treated under the same conditions with a spray dispersion which does not contain the active material.

The plant species tested, both crops and weeds, were the following:

| Graminaceous crops | |
|---|---|
| Wheat (*Triticum vulgare*) | WH |
| Maize (*Zea mays*) | MA |
| Rice (*Oryza sativa*) | RI |
| Dicotyledonous crops | |
| Groundnuts (*Arachis hypogea*) | GR |
| Rape (*Brassica napus*) | RA |
| Cotton (*Gossypium barbadenses*) | CT |
| Beans (*Phaseolus vulgaris*) | BE |
| Soya (*Glycine max*) | SO |
| Sunflower (*Helianthus annuus*) | SF |
| Graminaceous weeds | |
| Wild oat (*Avena fatua*) | WO |
| Crabgrass (*Digitaria sanguinalis*) | CG |
| Panick grass (*Echinochloa crus-galli*) | PA |
| Raygrass (*Lolium multiflorum*) | RA |
| Foxtail (*Setaria faberii*) | FX |
| Slender foxtail (*Alopecurus myosuroides*) | SFX |
| Dicotyledonous weeds | |
| Goosefoot (*Chenopodium album*) | GF |
| Nightshade (*Solanum nigrum*) | NI |
| Mustard (*Sinapis arvensis*) | MU |
| Chickweed (*Stellaria media*) | CW |

The results found, which are recorded in the table below, are expressed as the percentage destruction of the treated plants relative to an untreated reference sample.

The number 100 indicates that there is complete destruction of the plant in question. The results found are given in the table which follows:

| | Dose in | Graminaceous weeds | | | | | | Dicotyledonous weeds | | | | Graminaceous crops | | | Dicotyledonous crops | | | | | |
|---|---|---|---|---|---|---|---|---|---|---|---|---|---|---|---|---|---|---|---|---|
| No | kg/ha | WO | CG | PA | RA | FX | SFX | GF | NI | MU | CW | WH | MA | RI | GR | RA | CT | BE | SO | SF |
| 2 | 4 | 60 | — | 90 | 85 | — | 95 | 0 | — | 0 | — | 15 | 0 | 70 | — | 0 | 0 | 0 | — | 0 |
|  | 2 | 60 | 80 | 100 | 98 | 30 | 90 | 15 | — | 0 | 0 | 10 | 0 | 80 | 0 | 10 | 0 | 0 | 0 | 0 |
| 3 | 4 | 80 | 98 | 100 | 100 | 80 | 100 | 80 | — | 10 | 50 | 80 | 0 | 95 | 0 | 25 | 0 | 0 | 0 | 0 |
|  | 8 | 95 | 100 | 100 | 100 | 100 | 100 | 85 | — | 20 | 80 | 100 | 0 | 100 | 0 | 30 | 0 | 0 | 0 | 20 |
| 5 | 4 | 80 | 100 | 100 | 100 | 80 | 100 | 80 | 20 | 0 | 0 | 70 | 0 | 70 | 20 | 0 | 0 | 0 | 0 | 0 |
| 6 | 4 | 50 | 80 | 100 | 90 | 25 | 95 | 50 | 30 | 0 | 60 | 30 | 0 | 0 | 0 | 0 | 0 | 0 | 5 | 0 |
| 7 | 4 | 0 | 100 | 100 | 60 | 60 | 50 | 80 | 60 | 15 | 0 | 0 | 0 | 20 | 0 | 0 | 0 | 0 | 0 | 0 |
| 8 | 4 | 20 | 100 | 100 | 90 | 20 | 90 | 60 | 90 | 0 | 0 | 60 | 0 | 60 | 0 | 0 | 0 | 0 | 0 | 0 |
| 9 | 4 | 40 | 100 | 100 | 100 | 90 | 85 | 90 | 95 | 0 | 0 | 25 | 0 | 10 | 0 | 8 | 0 | 0 | 0 | 0 |
|  | 1 | 70 | 0 | 100 | 100 | 50 | 98 | 10 | — | 0 | 0 | 80 | 0 | 80 | 0 | 0 | 0 | 0 | 0 | 0 |
|  | 2 | 80 | 50 | 100 | 100 | 85 | 100 | 15 | — | 0 | 0 | 95 | 0 | 100 | 0 | 0 | 0 | 0 | 0 | 0 |
| 10 | 4 | 100 | 98 | 100 | 100 | 98 | 100 | 50 | — | 0 | 10 | 98 | 0 | 100 | 0 | 0 | 0 | 0 | 10 | 0 |
|  | 8 | 100 | 100 | 100 | 100 | 100 | 100 | 85 | — | 0 | 60 | 98 | 5 | 100 | 0 | 10 | 0 | 30 | 25 | 10 |
| 11 | 4 | 70 | 100 | 100 | 90 | 60 | 90 | 25 | 100 | 0 | 100 | 10 | 0 | 0 | 0 | 0 | 0 | 0 | 0 | 0 |
| 13 | 4 | 60 | 100 | 100 | 98 | 98 | 85 | 60 | — | 80 | 70 | 0 | 0 | 80 | — | 0 | 0 | 0 | — | 0 |
|  | 1 | 40 | 90 | 100 | 100 | 80 | 100 | 0 | 50 | 0 | 0 | 50 | 0 | 95 | 0 | 0 | 0 | 0 | 0 | 0 |
|  | 2 | 60 | 100 | 100 | 100 | 100 | 100 | 80 | 80 | 0 | 0 | 90 | 0 | 100 | 0 | 0 | 0 | 0 | 0 | 0 |
| 14 | 4 | 95 | 100 | 100 | 100 | 100 | 100 | 100 | 98 | 0 | 60 | 100 | 0 | 100 | 10 | 0 | 0 | 0 | 0 | 0 |
|  | 8 | 100 | 100 | 100 | 100 | 100 | 100 | 100 | 100 | 0 | 100 | 100 | 0 | 100 | 20 | 0 | 0 | 30 | 0 | 10 |
| 15 | 4 | 20 | 100 | 100 | 98 | 100 | 98 | 80 | 15 | 0 | 25 | 0 | 0 | 80 | — | — | 0 | 0 | 0 | 0 |
|  | 2 | 60 | 100 | 100 | 98 | 90 | 98 | 60 | 60 | 0 | 20 | 30 | 0 | 98 | 0 | 0 | 0 | 0 | 0 | 0 |
| 16 | 4 | 70 | 100 | 100 | 100 | 95 | 100 | 100 | 100 | 0 | 60 | 40 | 0 | 100 | 0 | 0 | 0 | 0 | 0 | 0 |
|  | 8 | 85 | 100 | 100 | 100 | 100 | 100 | 100 | 100 | 0 | 85 | 60 | 0 | 100 | 30 | 0 | 0 | 0 | 0 | 0 |
| 17 | 4 | 65 | 100 | 90 | 90 | 95 | 50 | 0 | 0 | 0 | 0 | — | — | — | — | — | — | — | — | — |
| 18 | 4 | 50 | 100 | 100 | 98 | 98 | 90 | 60 | 5 | 5 | 0 | 60 | 0 | — | — | 0 | — | — | — | — |
|  | 2 | 40 | 100 | 100 | 100 | 100 | 98 | 80 | 90 | 0 | 10 | 40 | 0 | 100 | 0 | 0 | 0 | 0 | 0 | 0 |
| 19 | 4 | 80 | 100 | 100 | 100 | 100 | 100 | 90 | 100 | 0 | 40 | 80 | 0 | 100 | 0 | 0 | 0 | 30 | 0 | 0 |
|  | 8 | 100 | 100 | 100 | 100 | 100 | 100 | 100 | 100 | 0 | 80 | 100 | 0 | 100 | 60 | 0 | 10 | 60 | 25 | 0 |
| 20 | 4 | 10 | 100 | 98 | 95 | 95 | 90 | 20 | 0 | 0 | 0 | 0 | 0 | 15 | — | 0 | 0 | 0 | 0 | 0 |
| 22 | 4 | 0 | 100 | 10 | 60 | 60 | 70 | 0 | 0 | 0 | 0 | 0 | 0 | 0 | — | 0 | 0 | 0 | 0 | 0 |
| 26 | 4 | 85 | — | 85 | 95 | — | 85 | 90 | — | 5 | 50 | 0 | 0 | 10 | — | 0 | 0 | 0 | — | 0 |
| 29 | 4 | 60 | 100 | 98 | 85 | 80 | 90 | 10 | 5 | 0 | 0 | 20 | 0 | — | — | 0 | — | — | — | — |
| 30 | 4 | 10 | — | 98 | 85 | — | 95 | 0 | — | 10 | 0 | 0 | 0 | 0 | — | 0 | 0 | 0 | — | 0 |
| 31 | 4 | 90 | 95 | 100 | 95 | 95 | 90 | 5 | 0 | 0 | 0 | 30 | 0 | — | — | 0 | — | — | — | — |
| 32 | 4 | 40 | 100 | 100 | 60 | 95 | 80 | 5 | 5 | 0 | 0 | 25 | 0 | — | — | 0 | — | — | — | — |
| 33 | 4 | 10 | 25 | 10 | 80 | 85 | 90 | 0 | 0 | 0 | 0 | 0 | 0 | 50 | — | 0 | 0 | 0 | 0 | 0 |
| 34 | 4 | 80 | 95 | 90 | 98 | 95 | 95 | 30 | 0 | 0 | 15 | 30 | 0 | — | — | 0 | — | — | — | — |
| 35 | 4 | 90 | 100 | 85 | 90 | 95 | 85 | 25 | 5 | 0 | 0 | 25 | 0 | — | — | 0 | — | — | — | — |
| 36 | 4 | 15 | — | 60 | 60 | — | 80 | 0 | — | 0 | — | 0 | 0 | 25 | — | 0 | 0 | 0 | — | 0 |
| 37 | 4 | 30 | 100 | 95 | 70 | 50 | 50 | 5 | 0 | 0 | 0 | — | — | — | — | — | — | — | — | — |
| 38 | 4 | 15 | 80 | 60 | 20 | 30 | 70 | 0 | 0 | 0 | 0 | — | — | — | — | — | — | — | — | — |
| 39 | 4 | 5 | 95 | 70 | 50 | 15 | 70 | 0 | 0 | 0 | 0 | — | — | — | — | — | — | — | — | — |
| 40 | 4 | 80 | 98 | 25 | 15 | 5 | 40 | 0 | 0 | 0 | 0 | 0 | 0 | — | — | 0 | — | — | — | — |
| 43 | 4 | 0 | — | 80 | 80 | — | 70 | 30 | — | 0 | 0 | 10 | 0 | 0 | — | 0 | 0 | 0 | — | 0 |
| 44 | 4 | 0 | — | 80 | 85 | — | 85 | 30 | — | 0 | 0 | 10 | 0 | 15 | — | 0 | 0 | 0 | — | 5 |
| 46 | 4 | 80 | 100 | 100 | 100 | 50 | 100 | 50 | 80 | 0 | 0 | 10 | 0 | 15 | 0 | 10 | 0 | 0 | 10 | 0 |
|  | 2 | 100 | 100 | 100 | 100 | 20 | 100 | — | 100 | 0 | 80 | 10 | 0 | 25 | 0 | 10 | 0 | 0 | 0 | 0 |
| 47 | 4 | 100 | 100 | 100 | 100 | 40 | 100 | — | 100 | 0 | 85 | 20 | 0 | 60 | 0 | 15 | 0 | 0 | 40 | 0 |
|  | 8 | 100 | 100 | 100 | 100 | 100 | 100 | — | 100 | 30 | 95 | 30 | 0 | 90 | 0 | 25 | 10 | 0 | 60 | 100 |
|  | 2 | 80 | 98 | 98 | 80 | 0 | 25 | — | 90 | 0 | 0 | 0 | 0 | 0 | 0 | 0 | 0 | 0 | 0 | 0 |
| 48 | 4 | 90 | 100 | 100 | 95 | 26 | 70 |  | 100 | 0 | 0 | 0 | 0 | 0 | 0 | 10 | 0 | 0 | 0 | 0 |
|  | 8 | 100 | 100 | 100 | 100 | 50 | 90 | — | 100 | 15 | 90 | 0 | 0 | 10 | 0 | 20 | 0 | 0 | 0 | 0 |
| 49 | 4 | 95 | 100 | 95 | 50 | 50 | 100 | 30 | 80 | 10 | 100 | 5 | 0 | 0 | 0 | 0 | 0 | 0 | 0 | 0 |
|  | 2 | 90 | 100 | 100 | 100 | 85 | 90 | 0 | 80 | 0 | 0 | 10 | 0 | 0 | 0 | 0 | 0 | 0 | 0 | 0 |
| 50 | 4 | 100 | 100 | 100 | 100 | 90 | 100 | 50 | 90 | 25 | 30 | 10 | 0 | 60 | 0 | 10 | 0 | 0 | 0 | 0 |
|  | 8 | 100 | 100 | 100 | 100 | 100 | 100 | 70 | 100 | 80 | 70 | 15 | 0 | 95 | 0 | 40 | 0 | 0 | 0 | 10 |
| 51 | 4 | 100 | 95 | 100 | 100 | 15 | 100 | 0 | 95 | 0 | 0 | 90 | 0 | 15 | 0 | 0 | 15 | 0 | 0 | 0 |
| 52 | 4 | 95 | 100 | 98 | 100 | 30 | 100 | 0 | 0 | 0 | 0 | 15 | 0 | 40 | 0 | 0 | 10 | 0 | 0 | 0 |
| 53 | 4 | 100 | 100 | 100 | 95 | 20 | 100 | 80 | 100 | 0 | 100 | 30 | 0 | 0 | 0 | 10 | 0 | 0 | 0 | 0 |
| 54 | 4 | 90 | 90 | 70 | 85 | 5 | 90 | 0 | 30 | 0 | 10 | 0 | 0 | 0 | 30 | 0 | 0 | 0 | 5 | 0 |
| 55 | 4 | 60 | 100 | 100 | 100 | 80 | 100 | 60 | 0 | 10 | 50 | 80 | 10 | 80 | 0 | 0 | 0 | 0 | 0 | 0 |
|  | 2 | 15 | 100 | 100 | 95 | 80 | 90 | — | 100 | 0 | 80 | 15 | 0 | 0 | 0 | 10 | 0 | 0 | 0 | 0 |
| 56 | 4 | 30 | 100 | 100 | 100 | 95 | 100 | — | 100 | 20 | 95 | 20 | 0 | 20 | 0 | 15 | 0 | 0 | 0 | 0 |
|  | 8 | 98 | 100 | 100 | 100 | 98 | 100 | — | 100 | 60 | 100 | 40 | 0 | 50 | 10 | 50 | 0 | 0 | 20 | 0 |
| 57 | 4 | 25 | 100 | 90 | 80 | 10 | 60 | 20 | 90 | 0 | 10 | 0 | 0 | 0 | 0 | 0 | 0 | 0 | 0 | 0 |
|  | 2 | 10 | 80 | 98 | 90 | 80 | 60 | — | 100 | 0 | 80 | 10 | 0 | 0 | 0 | 15 | 0 | 0 | 0 | 0 |
| 58 | 4 | 30 | 100 | 100 | 100 | 90 | 90 | — | 100 | 20 | 90 | 25 | 0 | 5 | 0 | 30 | 0 | 0 | 0 | 0 |
|  | 8 | 80 | 100 | 100 | 100 | 100 | 100 | — | 100 | 50 | 100 | 60 | 0 | 15 | 25 | 50 | 0 | 50 | 50 | 30 |
| 59 | 4 | 60 | 100 | 100 | 100 | 80 | 100 | 80 | 90 | 0 | 60 | 80 | 0 | 80 | 0 | 0 | 0 | 0 | 0 | 0 |
|  | 2 | 10 | 90 | 90 | 60 | 80 | 85 | 0 | 100 | 0 | 90 | 0 | 0 | 0 | 0 | 0 | 0 | 0 | 0 | 0 |
| 60 | 4 | 40 | 100 | 100 | 90 | 85 | 90 | 0 | 100 | 0 | 100 | 0 | 0 | 0 | 0 | 5 | 0 | 0 | 0 | 0 |
|  | 8 | 85 | 100 | 100 | 98 | 100 | 100 | 50 | 100 | 0 | 100 | 15 | 0 | 0 | 0 | 15 | 0 | 0 | 0 | 0 |
| 61 | 1 | 100 | 100 | 100 | 100 | 85 | 100 | 30 | 0 | 0 | 0 | 30 | 0 | 100 | 0 | 0 | 0 | 0 | 0 | 0 |
|  | 4 | 100 | 100 | 100 | 100 | 100 | 100 | 80 | 30 | 0 | 60 | 80 | 0 | 100 | 0 | 0 | 0 | 0 | 0 | 0 |
| 62 | 1 | 85 | 100 | 100 | 100 | 80 | 100 | 10 | 10 | 0 | 0 | 30 | 0 | 70 | 0 | 0 | 0 | 0 | 0 | 0 |
|  | 4 | 100 | 100 | 100 | 100 | 100 | 100 | 80 | 40 | 10 | 30 | 50 | 0 | 100 | 0 | 0 | 0 | 0 | 30 | 0 |
| 63 | 4 | 100 | 100 | 100 | 100 | 70 | 100 | 70 | 10 | 0 | 0 | 90 | 0 | 95 | 0 | 10 | 0 | 0 | 0 | 0 |
| 64 | 4 | 90 | 100 | 100 | 100 | 30 | 100 | 70 | 0 | 0 | 0 | 0 | 0 | 25 | 0 | 0 | 0 | 0 | 0 | 10 |
| 66 | 4 | 100 | 100 | 100 | 100 | 80 | 100 | 80 | 80 | 0 | 60 | 60 | 0 | 90 | 15 | 0 | 0 | 0 | 0 | 0 |

| No | Dose in kg/ha | Graminaceous weeds | | | | | | Dicotyledonous weeds | | | | Graminaceous crops | | | Dicotyledonous crops | | | | | |
|----|---|----|----|----|----|----|-----|----|----|----|----|----|----|----|----|----|----|----|----|----|
|  |  | WO | CG | PA | RA | FX | SFX | GF | NI | MU | CW | WH | MA | RI | GR | RA | CT | BE | SO | SF |
| 67 | 4 | 100 | 100 | 100 | 100 | 50 | 100 | 60 | 0 | 0 | 0 | 0 | 0 | 50 | 0 | 0 | 0 | 0 | 0 | 0 |
| 68 | 4 | 100 | 95 | 100 | 100 | 15 | 100 | 0 | 95 | 0 | 0 | 90 | 0 | 15 | 0 | 0 | 15 | 0 | 0 | 0 |
| 69 | 4 | 90 | 100 | 100 | 100 | 90 | 90 | 60 | 20 | 0 | 70 | 0 | 0 | 20 | — | 0 | 0 | 0 | 20 | 0 |
| 70 | 4 | 100 | 100 | 100 | 100 | 100 | 100 | 90 | 20 | 0 | 85 | 85 | 0 | 100 | 0 | 0 | 0 | 0 | 0 | 0 |

These results show the good herbicidal action of the compounds according to the invention and their selectivity regarding the crops when they are applied before emergence or before sowing of the crops. In general, all of these compounds have a good herbicidal action on graminaceous weeds. Some of the compounds are also active on certain dicotyledonous weeds.

Particularly valuable results have been obtained in the case of the following compounds:

Compound no. 10: 3-methyl-isoxazol-5-yl-methyl N,N-diisopropyl-thiolcarbamate.

Compound no. 14: 3-ethyl-isoxazol-5-yl-methyl N,N-diisopropylthiolcarbamate.

Compound no. 47: isoxazol-3-yl-methyl N,N-di-(n-propyl)-thiolcarbamate.

Compound no. 3: 3-methyl-isoxazol-5-methyl N,N-di-(n-propyl)-thiolcarbamate.

Compound no. 16: 3-(n-propyl)-isoxazol-5-yl-methyl N,N-diisopropylthiolcarbamate.

Compound no. 19: 3-isopropyl-isoxazol-5-yl-methyl N,N-diisopropylthiolcarbamate.

Compound no. 50: isoxazol-3-yl-methyl N-ethyl-N-butyl-thiolcarbamate.

Compound no. 56: 5-methyl-isoxazol-3-yl-methyl N,N-di-(n-propyl)-thiolcarbamate.

Compound no. 60: 5-methyl-isoxazol-3-yl-methyl N,N-diisobutylthiolcarbamate.

Compound no. 61: isoxazol-3-yl-methyl N-isopropyl-N-isobutylthiolcarbamate.

Compound no. 62: isoxazol-3-yl-methyl N-propyl-N-sec.-butylthiolcarbamate.

Compound no. 63: isoxazol-3-yl-methyl N-methyl-N-isopropylthiolcarbamate.

Compound no. 70: 3-methyl-isoxazol-5-yl-methyl N-isopropyl-N-isobutyl-thiolcarbamate.

Thus, by way of example, at doses from 2 kg./ha., compound no. 14 effects 100% destruction of crabgrass, panickgrass raygrass, foxtail and slender foxtail, wild oat being a little less sensitive. At this same dose, it also destroys certain dicotyledonous weeds, such as goosefoot and nightshade. At a dose of 4 kg./ha., the compound is well tolerated by crops of maize, rape, cotton and sunflower.

For herbicidal treatment by means of the compounds according to the invention, the dose of active material to be used can vary from 0.5 to 10 kg./ha., depending on the compound used, the type of crop and the nature of the soil. Preferably, this dose is between about 1 kg./ha. and 4 kg./ha.

For use in practice, the compounds according to the invention are rarely employed alone. Most frequently, they form part of formulations which in general comprise a carrier and/or a surface-active agent acceptable to the plants, in addition to the active material according to the invention.

The term "carrier" in the sense of the present description denotes an organic or inorganic, natural or synthetic material with which the active material is associated in order to facilitate its application to the plant, to the seeds or to the soil, or to facilitate its transport or its handling. The carrier can be solid (clays, natural or synthetic silicates, resins, waxes, solid fertilisers and the like) or fluid (water, alcohols, ketones, petroleum fractions, chlorinated hydrocarbons and liquified gases).

The surface-active agent can be an emulsifier, dispersing agent or wetting agent, and each of these can be ionic or non-ionic. Examples which may be mentioned are salts of polyacrylic acids and of ligninsulphonic acids, and condensates of ethylene oxide with fatty alcohols, fatty acids or fatty amines.

The compositions according to the invention can be prepared in the form of wettable powders, dusting powders, granules, solutions, emulsifiable concentrates, emulsions, suspension concentrates and aerosols.

The wettable powders are usually prepared in such a way that they contain from 25 to 95% by weight of active material and they usually contain, in addition to a solid carrier, from 0 to 5% by weight of a wetting agent and from 3 to 10% by weight of one or more stabilizers and/or other additives, such as penetrating agents, adhesives or anti-caking agents, dyestuffs and the like. By way of example, the following is the composition of a wettable powder.

active material (compound no. 47): 50%
calcium lignosulphate (deflocculating agent): 5%
anionic wetting agent: 1%
anti-caking silica: 5%
kaolin (extender): 39%

The water-soluble powders are obtained by mixing from 20 to 95% by weight of active material, from 0 to 10% of an anti-caking extender and from 0 to 1% of a wetting agent, the remainder consisting of a water-soluble extender, principally a salt.

The following is an example of the composition of a water-soluble powder:

active material (compound no. 50): 70%
anionic wetting agent: 0.5%
anti-caking silica: 5%
sodium sulphate (soluble extender): 24.5%

The granules, which are intended to be put on the soil, are usually prepared in such a way that they between 0.1 and 2 mm in size, and they can be manufactured by agglomeration or impregnation. In general, the granules contain from 0.5 to 25% of active material and from 0 to 10% by weight of additives, such as stabilizers, slow-liberation modifiers, binders and solvents.

The emulsifiable concentrates which can be applied by spraying usually contain, in addition to the solvent and, where necessary, a co-solvent, from 10 to 50% by weight/volume of active material and from 2 to 20% by weight/volume of appropriate additives, such as stabilizers, penetrating agents, corrosion inhibitors, dyestuffs and adhesives.

By way of example, the following is the composition of an emulsifiable concentrate, the amounts being expressed in g./liter:

active material (compound no. 60): 400 g/l alkali metal dodecylbenzenesulphonate: 24 g/l
nonylphenol reacted with 10 molecules of ethylene oxide: 16 g/l
cyclohexanone: 200 g/l
aromatic solvent: q.s.p. 1 liter The suspension concentrates, which can also be applied by spraying, are prepared in such a way that a stable fluid product which does not settle out is obtaned, and they usually contain from 10 to 75% by weight of active material, from 0.5 to 15% by weight of surface-active agents, from 0.1 to 10% by weight of thixotropic agents, from 0 to 10% by weight of appropriate additives, such as anti-foaming agents, corrosion inhibitors, stabilizers, penetrating agents and adhesives, and, as a carrier, water or an organic liquid in which the active material is substantially insoluble: certain organic solid materials or inorganic salts can be dissolved in the carrier to assist in preventing sedimentation or to act as anti-freeze agents for the water.

Aqueous dispersions and aqueous emulsions, for example compositions obtained by diluting a wettable powder or an emulsifiable concentrate according to the invention with water, fall within the general scope of the present invention. The emulsions can be of the water-in-oil type or of the oil-in-water type and they can have a thick consistency such as that of a "mayonnaise".

The compositions according to the invention can contain other ingredients, for example protective colloids, adhesives or thickeners, thixotropic agents, stabilizers or sequestering agents, as well as other known active material possessing pesticidal properties, in particular possessing insecticidal or fungicidal properties.

We claim:

1. A compound of the formula:

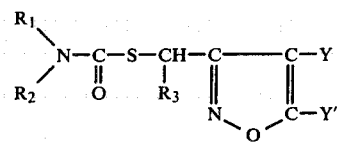

in which $R_1$ and $R_2$ are identical or different and each represents a linear or Branched alkyl radical containing 1 to 4 carbon atoms, cyclohexyl or methoxyethyl, $R_3$ is a hydrogen atom or methyl group and Y and Y' are identical or different and each represents a hydrogen or methyl group.

2. A compound according to claim 1, in which said thiolcarbamate is chosen from the group comprising: isoxazol-3-yl-methyl N,N-di-(n-propyl)-thiolcarbamate, isoxazol-3-yl-methyl N-ethyl-N-butyl-thiolcarbamate, 5-methyl-isoxazol-3-yl-methyl N,N-di-(n-propyl)-thiolcarbamate, 5-methyl-isoxazol-3-yl-methyl N,N-diisobutyl-thiolcarbamate, isoxazol-3-yl-methyl N-isopropyl-N-isobutyl-thiolcarbamate, isoxazol-3-yl-methyl N-propyl-N-sec.-butyl-thiolcarbamate and isoxazol-3-yl-methyl N-ethyl-N-isopropyl-thiolcarbamate.

3. A compound which is 3-methyl-isoxazol-4-yl-methyl N,N-di-propyl-thiolcarbamate.

4. A herbicidal composition comprising as the active material, at least one compound according to any of claims 1, 2 or 3 in an herbicidally effective amount in combination with inert an agriculturally acceptable carrier and/or agriculturally acceptable surface active agent.

5. A composition according to claim 4, in which said composition contains said active material in an amount of between 0.5 and 95% by weight and in which the composition contains at least one inert agriculturally acceptable carrier and/or surface-active agent.

6. Process for the selective destruction of weeds in a crop of maize, groundnuts, rape, cotton, beans, soya, sunflowers, wheat or rice which comprises applying to the locus of said crop before emergence or before sowing said crop an herbicidally effective amount of a composition according to claim 4.

* * * * *